(12) United States Patent
Conant et al.

(10) Patent No.: US 6,313,371 B1
(45) Date of Patent: Nov. 6, 2001

(54) FLATULENCE DEODORIZER (76) Inventors: Brian J Conant; Myra M Conant, both of 94-1068 Akaku St., Mililani, HI (US) 96789

( * ) Notice: Subject to any disclaimer, the term of this patent is extended or adjusted under 35 U.S.C. 154(b) by 0 days.

(21) Appl. No.: 09/548,097

(22) Filed: Apr. 12, 2000

(51) Int. Cl.⁷ ................................................... A61F 13/15
(52) U.S. Cl. ........................................................... 604/359
(58) Field of Search ................................... 604/359, 378

(56) References Cited

U.S. PATENT DOCUMENTS

| | | | |
|---|---|---|---|
| 2,690,415 | * | 9/1954 | Shuler ................................. 604/359 |
| 4,547,195 | * | 10/1985 | Jackson ............................... 604/359 |
| 4,715,857 | * | 12/1987 | Juhasz et al. ........................ 604/359 |
| 5,593,398 | * | 1/1997 | Weimer ............................... 604/359 |
| 5,665,081 | * | 9/1997 | Grosse ................................ 604/359 |

* cited by examiner

*Primary Examiner*—Dennis Ruhl
(74) *Attorney, Agent, or Firm*—Michael I. Kroll (57) ABSTRACT

The present invention 10 discloses a pad to be worn by a user 12 for absorbing gas due to flatulence. The pad is constructed of activated charcoal cloth 16 disposed between a pair of laminations or layers 18 having multiple perforations 20 therein. The method of use of the present invention is also simple. The pad 10 is non-intrusively taped inside briefs or panties 24 in the anal area using double-sided adhesive tape 28 and due to its slim profile, the wearer is comfortably unaware of its presence. A continuous roll or portion of double-sided tape 28 is provided with perforated section intended for tearing off for one time, disposable use with the washable and reusable filter pads 10. A double-compartment ziplocked plastic bag 33 is also provided for carrying and separating the tape and pads for sanitary purposes. This makes the present invention 10 a safe, effective, cost efficient, comfortable and least intrusive method of dealing with this embarrassing problem.

5 Claims, 9 Drawing Sheets

FLATULENCE DEODORIZER

BACKGROUND OF THE INVENTION

1. Field of the Invention

The present invention relates generally to intestinal discharge control products and, more specifically, to flatulence deodorizers. There are various devices in this field for dealing with the problems of intestinal discharges with some degree of success. However, all of them are somewhat cumbersome and/or bulky to use. The present invention, the Flatulence Deodorizer, is the first product for this application to use activated charcoal cloth as a deodorizer because it is so much more effective in removing odor than other known agents and because of its highly efficient filtering action, the thickness of the cloth can be significantly reduced without loosing effectiveness. The filter is worn taped to the inside of briefs or panties and because of its slim profile, the wearer is comfortable and virtually unaware of its presence. The activated charcoal cloth filter is also washable and reusable. This makes the present invention the most effective, cost efficient, comfortable and least intrusive means of deodorizing gassy discharges.

2. Description of the Prior Art

There are other protective devices designed for shielding against, filtering and/or capturing intestinal exudations of various kinds. Typical of these is U.S. Pat. No. 4,182,335 issued to C. James Matrullo on Jan. 8, 1980.

Another patent was issued to Randolph E. Campbell on Dec. 25, 1984 as U.S. Pat. No. 4,490,145. Yet another U.S. Pat. No. 4,880,417 was issued to Alexander A. Yabrov on Nov. 14, 1989 and still yet another was issued on Nov. 1, 1994 to David W. Revelle as U.S. Pat. No. 5,360,421.

Another patent was issued to Kenneth J Grosse on Sep. 9, 1997 as U.S. Pat. No. 5,665,081. Yet another U.S. Pat. No. 5,728,080 was issued to Masuhiro Suyama on Mar. 17, 1998. Another was issued to Barbara Oakley Sauer on Sep. 28, 1999 as U.S. Pat. No. 5,957,907.

U.S. Pat. No. 4,182,335

Inventor: C. James Matrullo

Issued: Jan. 8, 1980

An anal filter for protecting underwear from soiling, is attached to a person's anus solely be non-adhesive adherence to the anus and adjacent portions of the buttocks, due to a facing of fluffy fibrous material, and when attached, serves as a filter by being pervious to the discharge of gas through the anus but substantially impervious to complete passage of excreta carried by the gas or remaining on the anus from a bowel movement. A layer may be adhesively secured to the fibrous material and which prior to use of the anal filter can be pulled off from the fibrous material while pulling this material's fibers outwardly so as to give the material its fluffy characteristic.

U.S. Pat. No. 4,490,145

Inventor: Randolph E. Campbell

Issued: Dec. 25, 1984

An ostomy pouch having a filter element affixed to the outer pouch wall. The outer pouch wall has an aperture and the filter element includes a polymeric film cover and an insert of gas deodorizing material. The film cover also has an aperture and opposite ends of the insert overlie the two apertures.

U.S. Pat. No. 4,880,417

Inventor: Alexander A. Yabrov

Issued: Nov. 14, 1989

An anal pad for preventing soiling of underwear due to undesired anal discharge. The anal pad includes a thin outer shell enclosing a semi-rigid shell. The semi-rigid shell may be a layer on one interior surface of the outer shell and may also partially cover the opposite interior surface of the outer shell. An absorbing layer is located within the outer shell and the semi-rigid layer. The absorbing layer contains glycerin which absorbs hydrogen sulfide gas and the combination of the absorbing layer and the semi-rigid shell acts as a sound muffling camera so as to decrease the noise due to flatus. The absorbing layer is made of a light porous materials, the semi-rigid layer is made of compressed paper and the outer shell is made of a thin sheet of lignin paper. A layer of glue is provided on the outer surface of the anal pad for attaching it to a user's underwear.

U.S. Pat. No. 5,360,421

Inventor: David W. Revelle

Issued: Nov. 1, 1994

A washable and reusable absorbent garment designed to be fitted about the waist and legs and covering the groin and anal areas of a wearer. The garment includes a number of superimposed layers of textile material sewn together along their edges. Elastic material may be sewn in the material around the leg openings and waist to improve the fit. A liner material covers the inner surface of the garment. The liner layer of the garment or that portion which is next to the wearer's skin is a knitted bicomponent textile comprised of a brushed polyester outer layer which is interknitted with a nylon block co-polymer inner layer. The materials function to transfer moisture in both vapor and liquid form from the polyester side to the nylon side where it is dispersed and made available to the garment's second or absorbent layer. The two specific materials in the liner adjacent the wearer's skin and absorbent material work together to maintain a high degree of comfort for the wearer even after it has been wetted. The structural and functional integrity of the garment is maintained after repeated washings.

U.S. Pat. No. 5,665,081

Inventor: Kenneth J. Grosse

Issued: Sep. 9, 1997

A pad for attenuating sound and absorbing odors from an anal region of an individual. The inventive device includes a pad member containing a volume of odor-absorbing granulated charcoal covered by a layer of filler material and encapsulated with a flexible web. A gluteus insert extends from the pad for positioning between the gluteus-maximus muscles and against the anal region of the user to attenuate noise emanating therefrom.

U.S. Pat. No. 5,728,080

Inventor: Masuhiro Suyama

Issued: Mar. 17, 1998

The present invention relates to a degassing device for an artificial anal bag which is capable of storing the gas generated in the intestines, and of discharging the gas from the bag at a selected place where degassing causes no nuisance to others.

It comprises an elongated tube having a filter loaded therein, an opening-and-closing plug attached to its head end and a diverging joint formed at its tail end. The diverging joint can be attached to the circumference of a joint opening, which is made in the upper part of the bag.

When the bag is inflated with gas and excreta from the intestines, the patient can go to the men's room or somewhere for discharging the gas from the bag. Then, the excreta and liquid content are prevented from passing through the filter, only permitting the gas to flow therethrough. Thus, degassing can be put under the perfect control by the patient, so that there is no fear of permitting leakage of gas to cause nuisance to others or imprignation of his underwear with unpleasant odor before the patient is aware.

U.S. Pat. No. 5,957,907

Inventor: Barbara Oakley Sauer

Issued: Sep. 28, 1999

An absorbent article includes a close fitting bodyside liner having an opening therein. The opening defines a front end edge, a rear end edge, and a pair of laterally opposed side edges. The article also includes a pair of elastic members which extend longitudinally beyond at least one of the end edges of the opening in a laterally divergent direction. The elastic members may also extend at least partially along the side edges of the opening. The elastic members are configured to maintain the edges of the opening in contact with the wearer's buttocks and align the opening with the wearer's anal opening in use. The article may further include a liquid management material located on the bodyside liner in the front waist to absorb or contain liquid exudates.

While these devices may be suitable for the purposes for which they were designed, they would not be as suitable for the purposes of the present invention, as hereinafter described.

SUMMARY OF THE PRESENT INVENTION

The present invention discloses a pad to be worn by a user for absorbing gas due to flatulence. The pad is constructed of activated charcoal cloth disposed between a pair of laminations or layers having multiple perforations therein. Activated charcoal cloth was originally developed by the British Chemical Defense Establishment of the Ministry of Defense as a highly efficient filter medium for protection against nerve gas and other highly toxic vapors which might be used in chemical warfare. This is the reason for its outstanding advantage as a decontaminating material in commercial air and water purification applications. Activated charcoal cloth is 100% activated charcoal produced in a flexible textile form and adsorbs more effectively than granular forms of activated charcoal due to its microporous character and higher internal surface area compared to the granular form. Because activated charcoal cloth is so much more effective per unit area in removing odor than other known agents, the thickness of the cloth can be significantly reduced without loosing effectiveness. The method of use of the present invention is also simple: it is non-intrusively taped inside briefs or panties in the anal area using double-sided adhesive tape and due to its slim profile, the wearer is comfortably unaware of its presence. A continuous roll or portion of double-sided tape is provided with perforated section intended for tearing off for one time, disposable use with the washable and reusable filter pads. A double-compartment ziplocked plastic bag is also provided for carrying and separating the tape and pads for sanitary purposes. This makes the present invention a safe, effective, cost efficient, comfortable and least intrusive method of dealing with this embarrassing problem.

A primary object of the present invention is to provide a wearable means of deodorizing intestinal gas that will be most effective.

Another object of the present invention is to provide a wearable means of deodorizing intestinal gas that will be least intrusive.

Yet another object of the present invention is to provide a wearable means of deodorizing intestinal gas that will be easy to use.

Still yet another object of the present invention is to provide a wearable means of deodorizing intestinal gas that will be comfortable for the wearer.

Yet another object of the present invention is to provide a wearable means of deodorizing intestinal gas that will be washable and reusable.

Yet another object of the present invention is to provide a means of deodorizing intestinal gas that will be inexpensive to purchase.

Additional objects of the present invention will appear as the description proceeds.

The present invention overcomes the shortcomings of the prior art by providing the present invention, the Flatulence Deodorizer, the first product of its kind to use activated charcoal cloth as a deodorizer for this application. Activated charcoal cloth was originally developed by the British Chemical Defense Establishment of the Ministry of Defense as a highly efficient filter medium for protection against nerve gas and other highly toxic vapors which might be used in chemical warfare. This is the reason for its outstanding advantage as a decontaminating material in commercial air and water purification applications. ACC is 100% activated charcoal produced in a flexible textile form and adsorbs more effectively than granular forms of activated charcoal due to its microporous character and higher internal surface area compared to the granular form. Because activated charcoal cloth is so much more effective per unit area in removing odor than other known agents, the thickness of the cloth can be significantly reduced without loosing effectiveness. The method of application of the present invention is also simple: it is non-intrusively taped inside briefs or panties using double-sided adhesive tape and due to its slim profile, the wearer is comfortably unaware of its presence. A continuous roll or portion of double-sided tape is provided with perforated sections intended for tearing off for one time, disposable use with the washable and reusable filter pads. A double-compartment ziplocked plastic bag is also provided for carrying and separating the tape and pads for sanitary purposes. This makes the present invention a safe, effective, cost efficient, comfortable and least intrusive method of dealing with this embarrassing problem.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the following numbering is used throughout the drawing.

10 present invention
12 user
14 odor or gas
16 activated charcoal cloth
18 cloth layers
20 perforations
22 buttocks
24 brief
26 contour of buttock
28 double sided tape
30 removable protective layer
31 perforations
32 single application length
33 bag
34 compartment for pads
36 compartment for adhesive
38 elongated end
40 enlarged end

DESCRIPTION OF THE PREFERRED EMBODIMENT(S)

In order that the invention may be more fully understood, it will now be described, by way of example, with reference to the accompanying drawings in which FIGS. 1 through 9 illustrate the present invention being a flatulence deodorizer.

Figure 1:
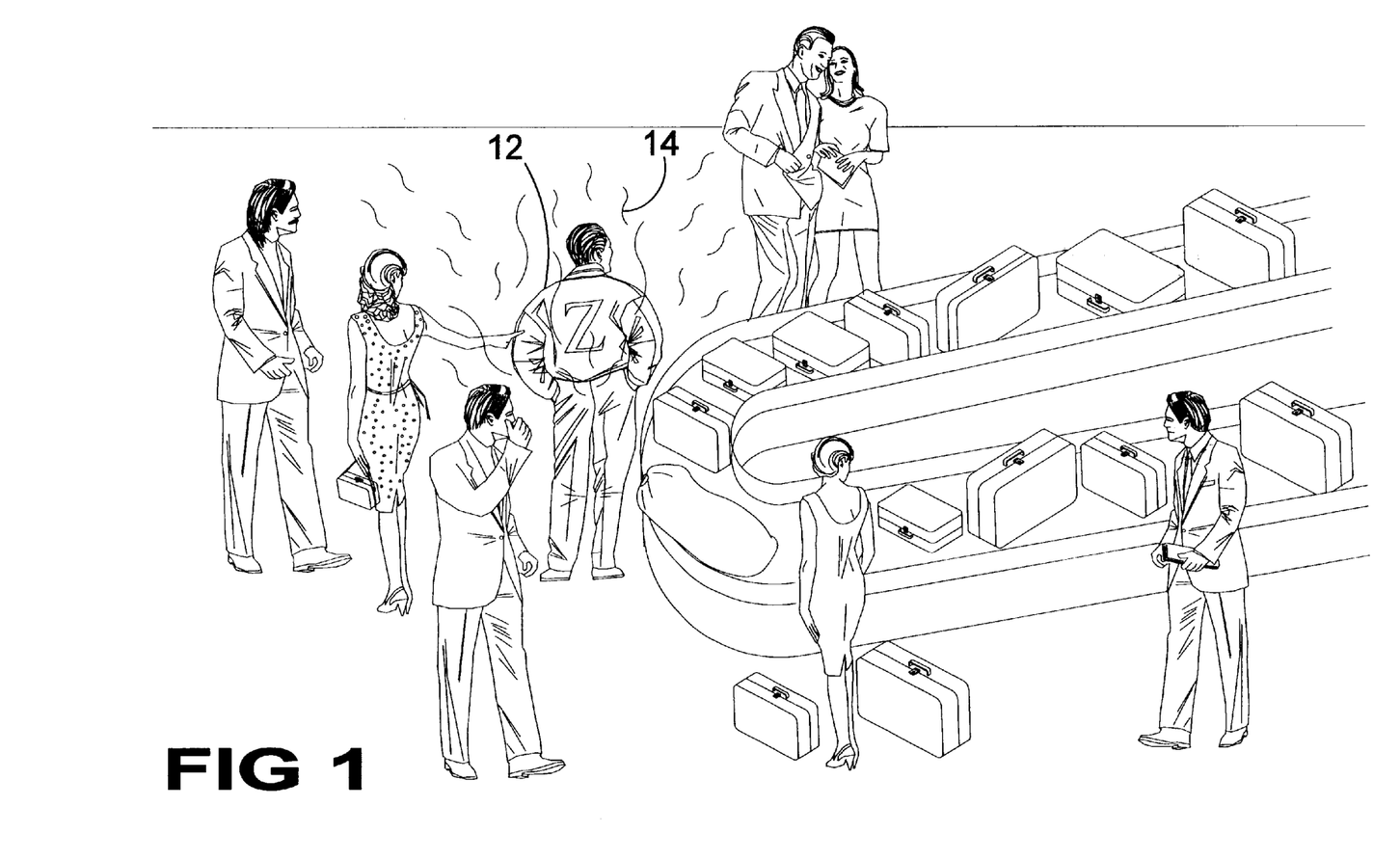
FIG. 1 is a perspective view of a scenario illustrating the embarrassing and unpleasant effects of uncontrolled flatus odor in a social situation.

Turning to FIG. 1, shown therein is a perspective view of a scenario illustrating the embarrassing and unpleasant effects upon a potential user 12 of uncontrolled flatus gas or odor 14 in a social situation.

Figure 2:
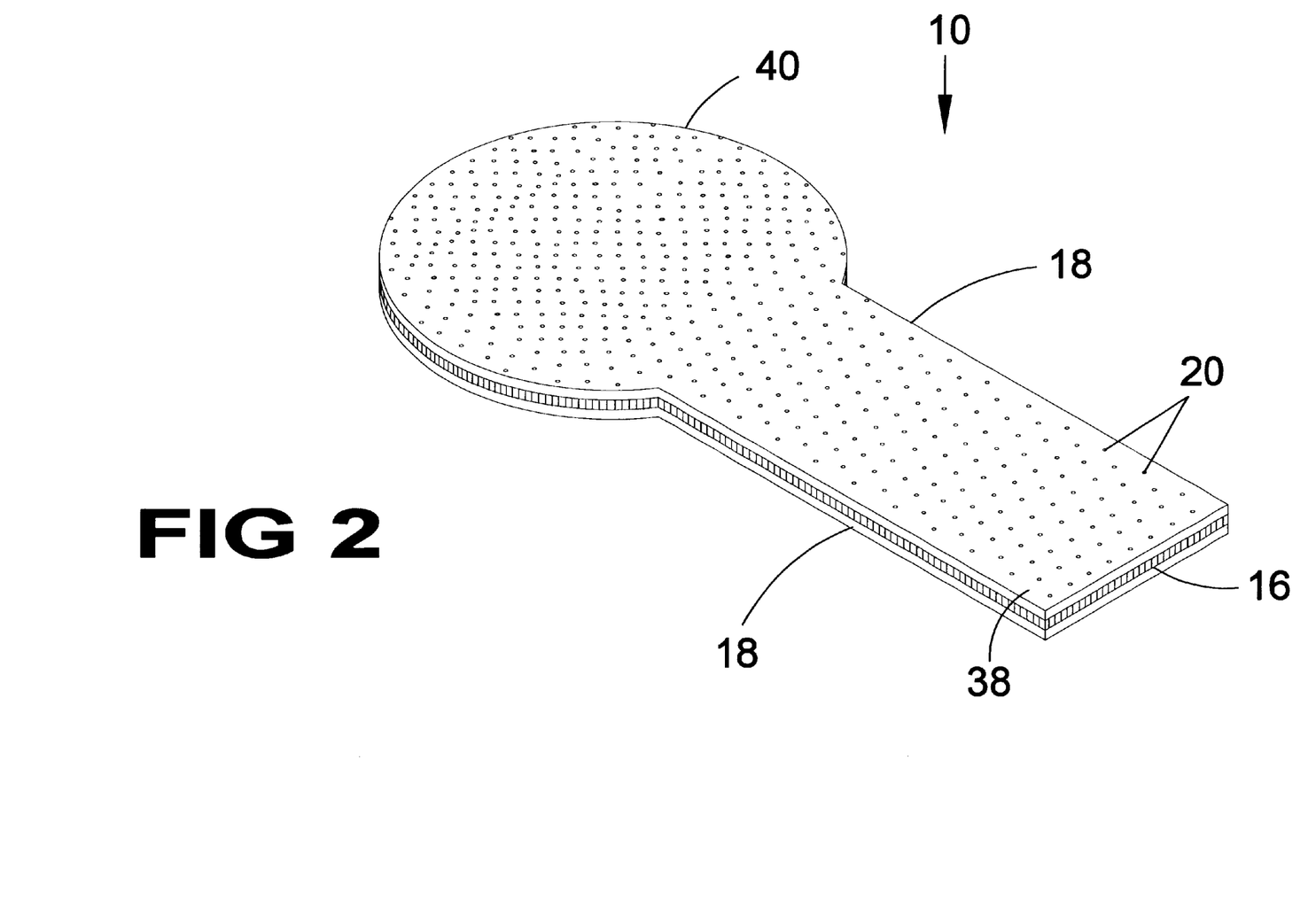
FIG. 2 is a perspective view of the activated charcoal cloth filter assemblage of the present invention.

Turning to FIG. 2, shown therein is a perspective view of the activated charcoal cloth filter assemblage of the present invention 10. Shown is the activated charcoal cloth 16 disposed between a pair of cloth layers or laminations 18 having multiple perforations 20 therein. The pad 10 has a first elongated end 38 and a second circular-shaped enlarged end 40 sized to cover the anal area of a user.

Figure 3:
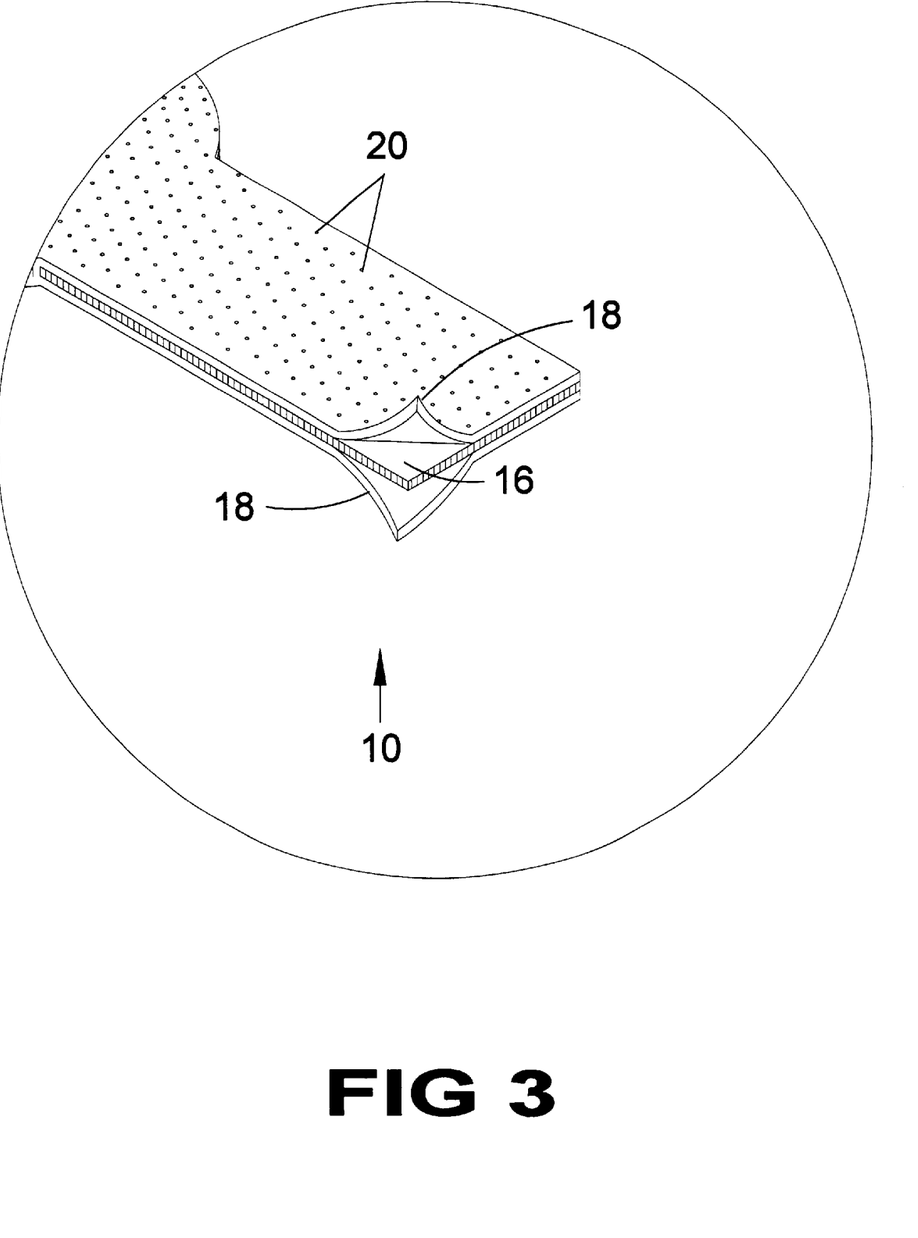
FIG. 3 is a perspective view of the activated charcoal cloth filter assemblage of the present invention showing the 3 laminated layers separated.

Turning to FIG. 3, shown therein is a perspective view of the present invention 10 showing the activated charcoal cloth 16 and the two outer laminated layers 18 showing the three separate layers 16, 18 along with perforations 20.

Figure 4:
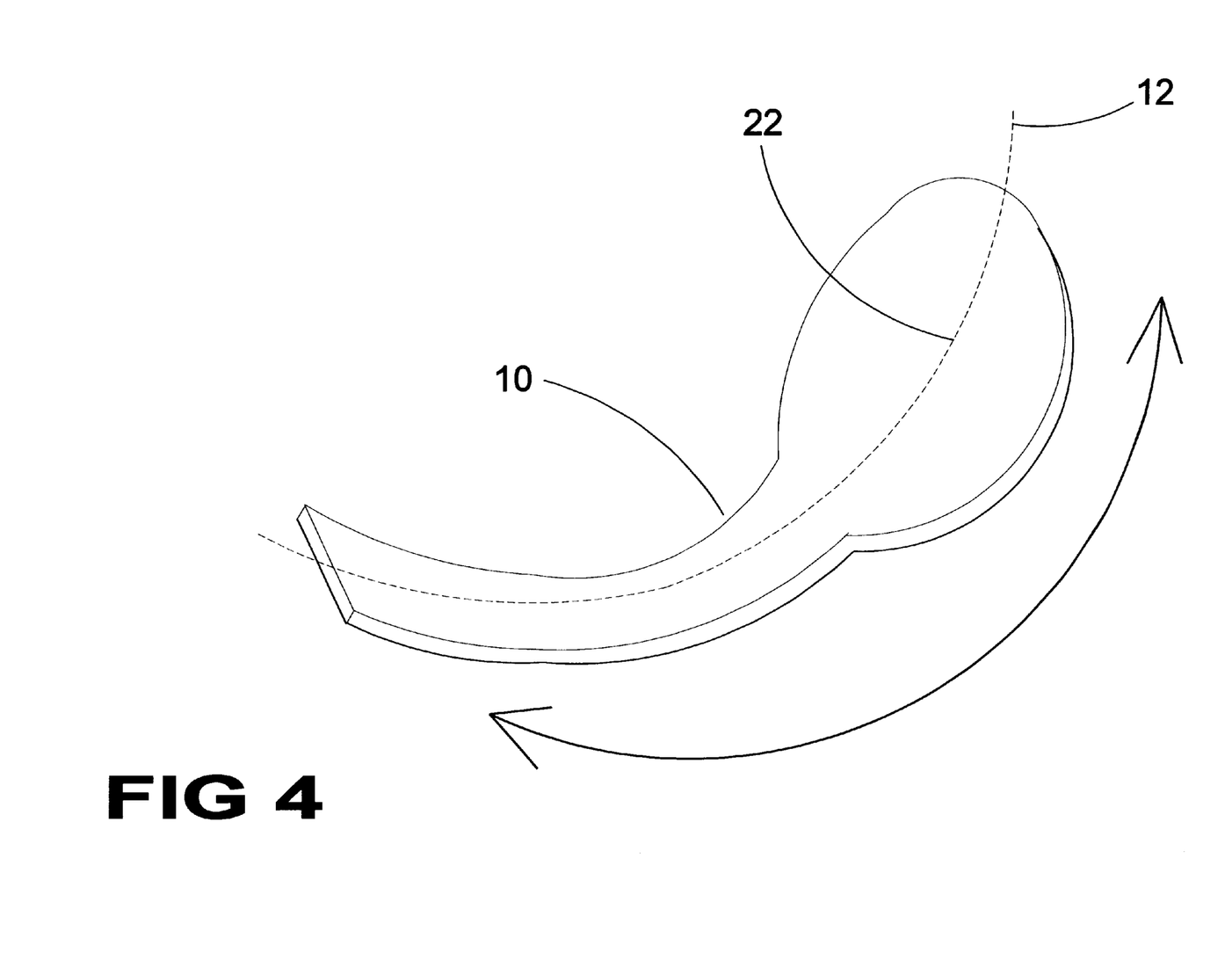
FIG. 4 is a perspective view of the activated charcoal cloth filter of the present invention showing the contour of the filter when worn.

Turning to FIG. 4, shown therein is a perspective view of the activated charcoal cloth filter of the present invention 10 showing the contour of the filter when worn. Shown is the contour of the user's buttock 22 with the present invention 10 conforming thereto. The enlarged end 40 of the present invention 10 is placed near the anus of the user 12.

Figure 5:
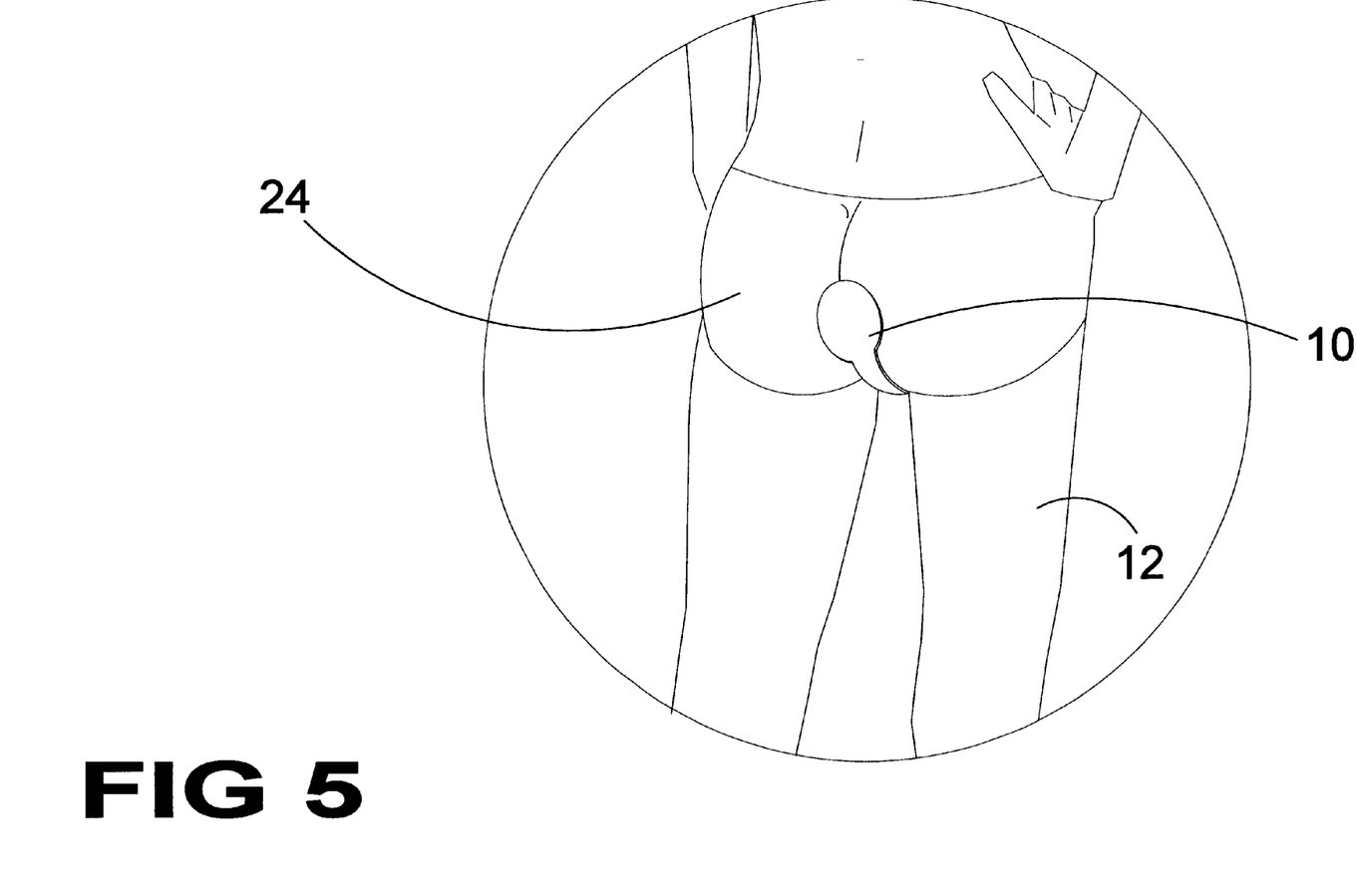
FIG. 5 is a perspective view of a typical user of the present invention showing the appropriate placement and configuration of the filter inside the briefs or panties of the wearer.

Turning to FIG. 5, shown therein is a perspective view of a typical user 12 of the present invention 10 showing the appropriate placement and configuration of the filter inside the briefs or panties 24 of the user 12.

Figure 6:
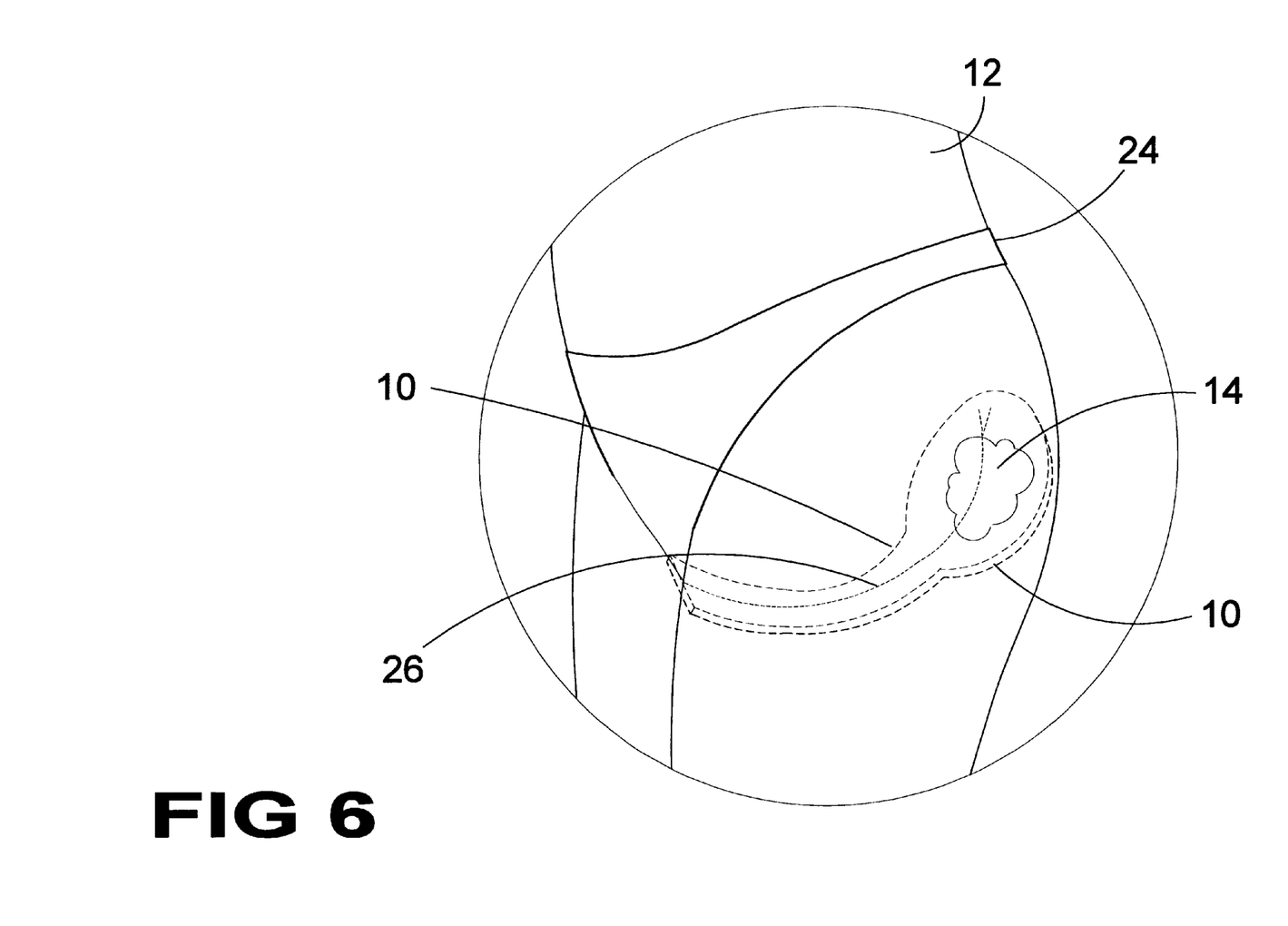
FIG. 6 is a perspective view of a typical user of the present invention illustrating its function inside the briefs or panties of the wearer.

Turning to FIG. 6, shown therein is a perspective view of a typical user 12 of the present invention 10 illustrating its function inside the briefs or panties 24 of the wearer. Also shown is flatulent gas 14 trapped in pad 10 along with the contour of the buttock 26.

Figure 7:
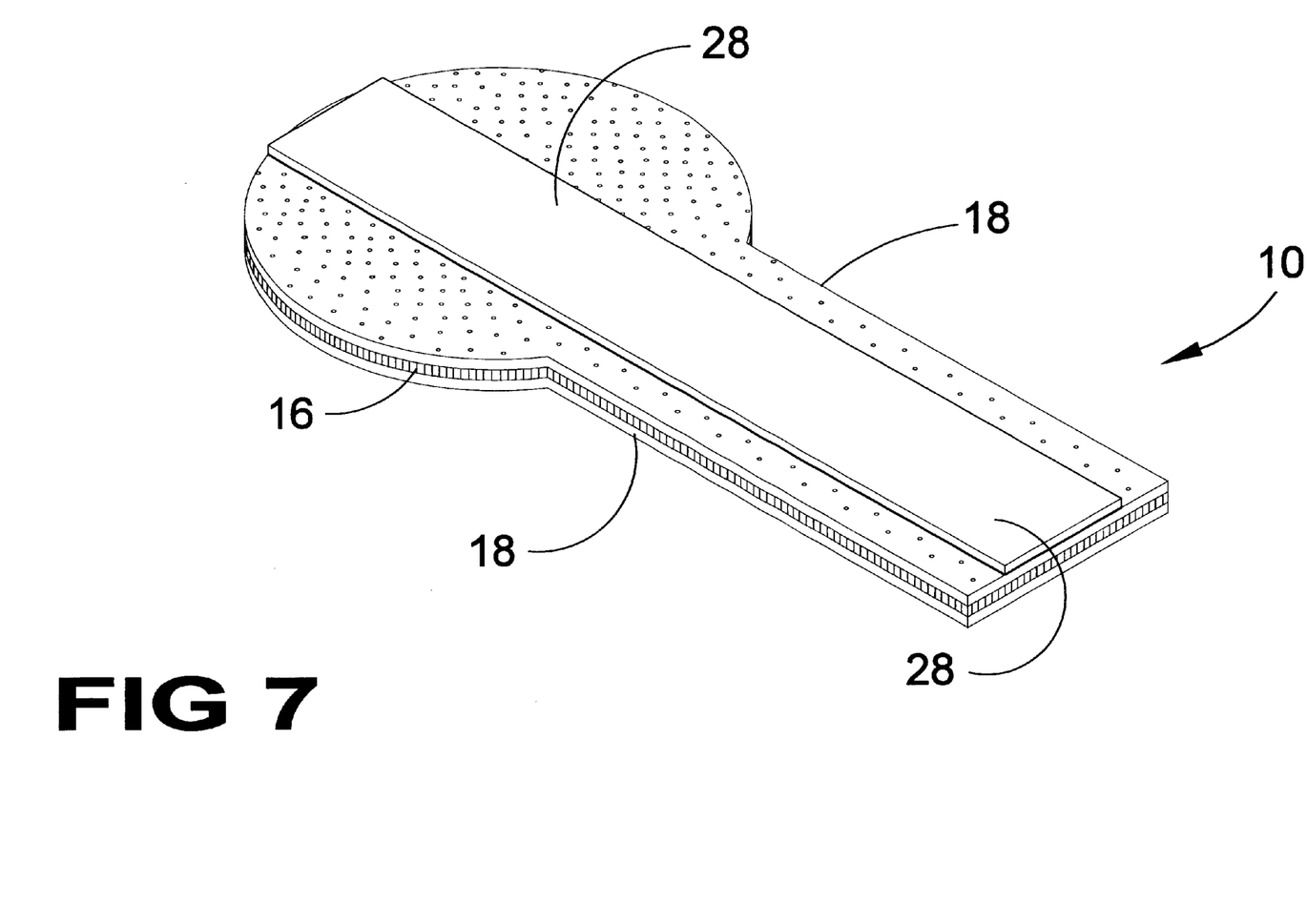
FIG. 7 is a perspective view of the present invention showing the double-sided tape attached for adhering to the inside the briefs or panties of the wearer.

Turning to FIG. 7, shown therein is a perspective view of the present invention 10 showing the double-sided tape 28 attached thereto for adhering to the inside of the briefs or panties of the wearer. Also shown is the charcoal cloth 16 and laminations 18.

Figure 8:
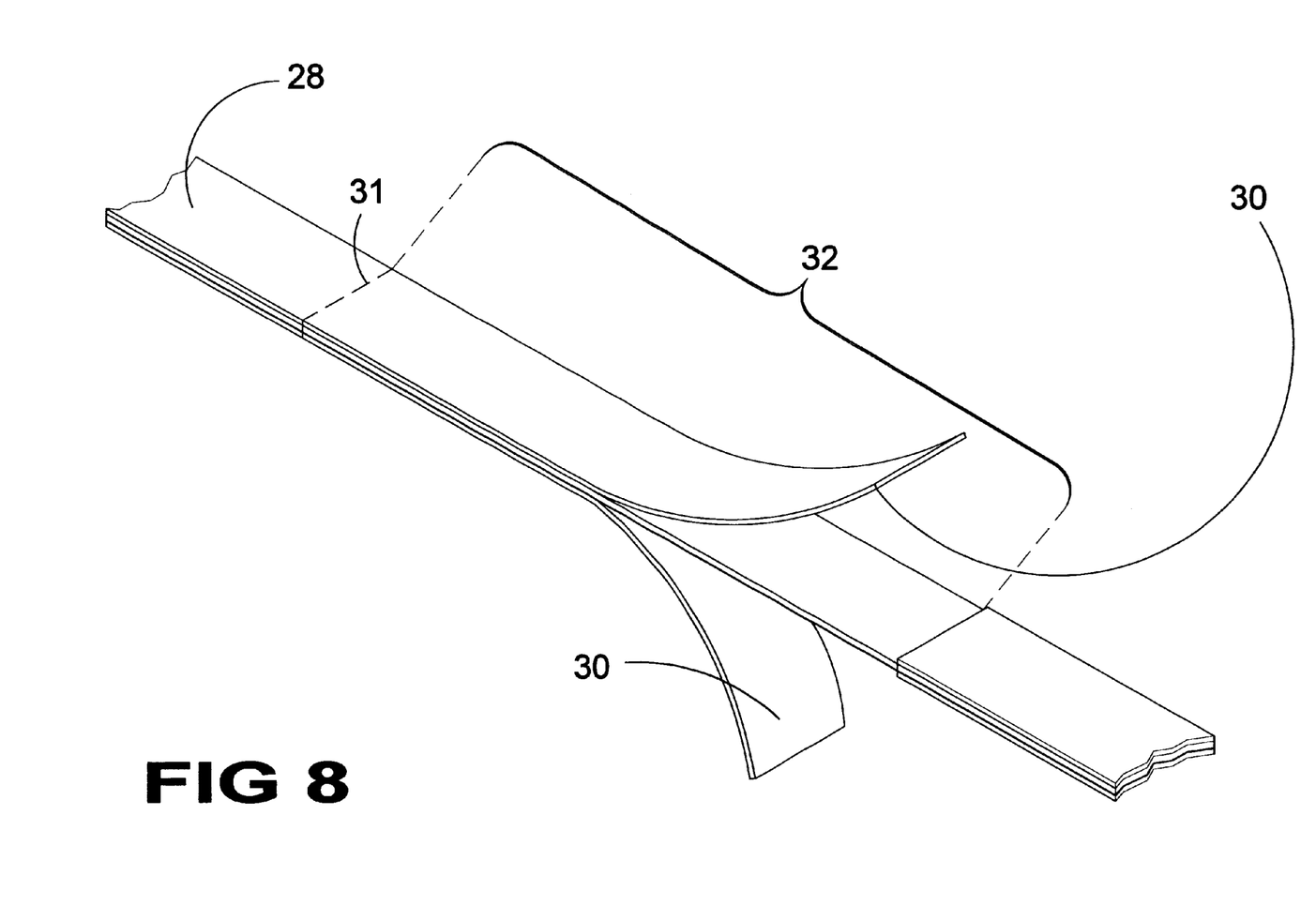
FIG. 8 is a perspective view of the continuous strip of double-sided tape with perforated single use sections of the present invention.

Turning to FIG. 8, shown therein is a perspective view of the continuous strip of double-sided tape 28 with multiple transverse perforated 31 single use, removable sections 30 of the present invention illustrating a single application length 32 of tape.

Figure 9:
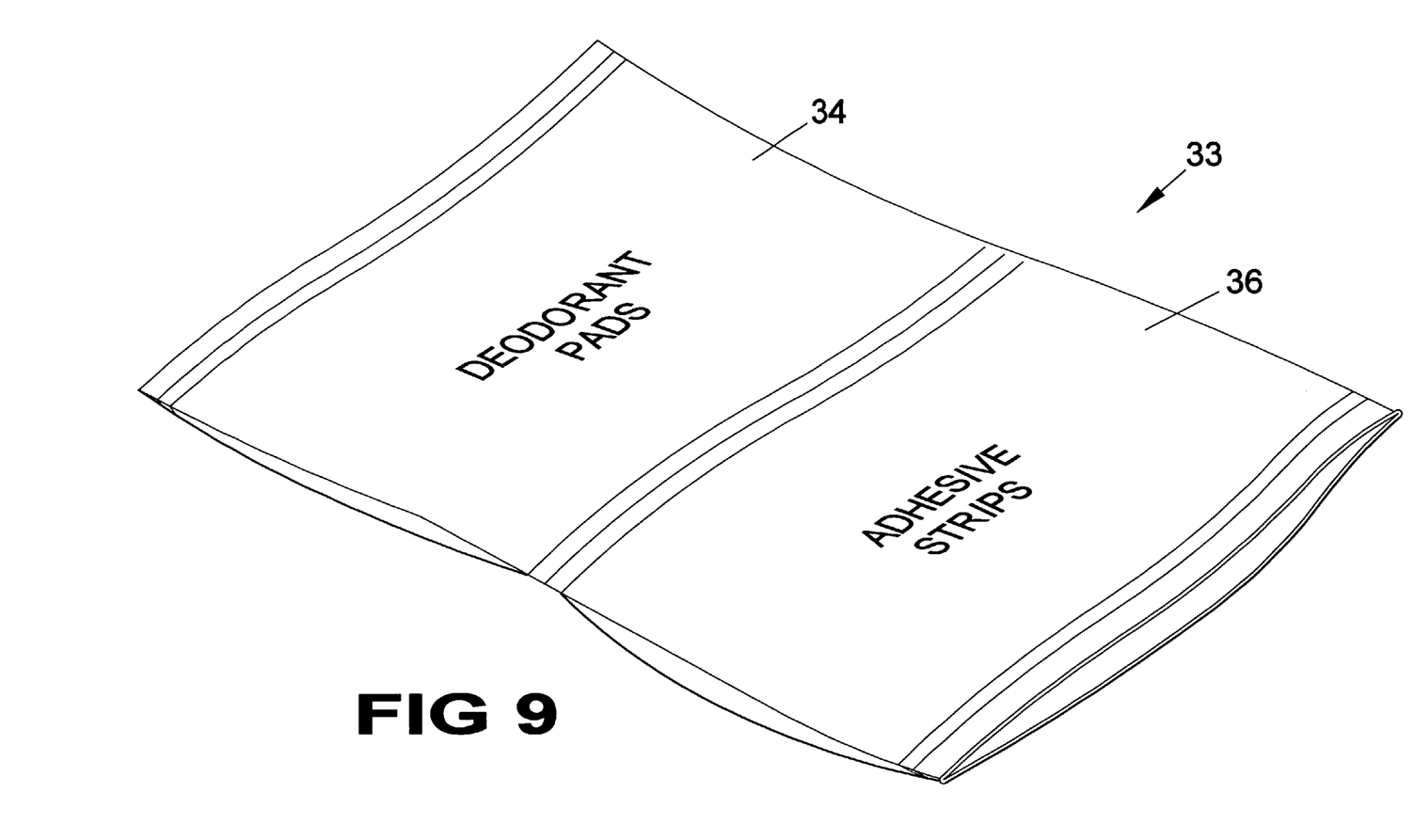
FIG. 9 is a perspective view of the double-compartment ziplocked plastic bag provided by the present invention for keeping unused continuous double-sided tape and filter pads separated for sanitary purposes.

Turning to FIG. 9, shown therein is a perspective view of the double-compartment ziplocked plastic bag 33 provided by the present invention for keeping unused continuous double-sided tape and filter pads separated for sanitary purposes. A first compartment holds deodorant pads 34 and the second compartment holds adhesive strips 36.

What is claimed is:

1. An apparatus for absorbing flatulence odor to be worn close to the body of a user, comprising:
    a) a pad having a first elongated end and a second enlarged end, said enlarged end being circular in shape;
    b) a first layer of activated charcoal cloth interior of said pad;
    c) a second layer and a third layer of cloth laminated to said first layer of activated charcoal cloth to form said pad;

d) said second layer and said third layer of cloth having a plurality of perforations therein;

e) said pad conforming to the shape of the body of a user; and, f) means for attaching said pad to the underwear of the user.

2. The apparatus of claim 1, wherein said activated charcoal cloth further comprises activated charcoal produced in a flexible textile form.

3. The apparatus of claim 1, further comprising double-sided tape having a first adhesive side and a second adhesive side, said first adhesive side attached to said pad.

4. The apparatus of claim 1, wherein said pad is washable and reusable.

5. A kit for absorbing flatulence odor to be worn close to the body of a user comprising:

a) a pad having a first elongated end and a second enlarged end, said enlarged end being circular in shape;

b) a first layer of activated charcoal cloth interior of said pad;

c) a second layer and a third layer of cloth laminated to said first layer of activated charcoal cloth to form said pad;

d) said second layer and said third layer of cloth having a plurality of perforations therein;

e) said pad conforming to the shape of the body of a user;

f) means for attaching said pad to the underwear of the user;

g) a roll of continuous strip of double-sided tape having multiple transverse perforations thereon, said perforations being placed at intervals thereby forming single pieces of tape sized for convenient use with said pad; and h) a plastic bag for containing said pad and said roll of double-sided tape, said bag having a first compartment for containing said roll of double-sided tape and a second compartment for containing said pad.

* * * * *